(12) United States Patent
Honda et al.

(10) Patent No.: US 9,636,160 B2
(45) Date of Patent: May 2, 2017

(54) IMPLANT

(71) Applicant: OLYMPUS CORPORATION, Tokyo (JP)

(72) Inventors: Jun Honda, Tokyo (JP); Takamitsu Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/378,558

(22) Filed: Dec. 14, 2016

(65) Prior Publication Data

US 2017/0086897 A1   Mar. 30, 2017

Related U.S. Application Data

(63) Continuation of application No. PCT/JP2015/054322, filed on Feb. 17, 2015.

(30) Foreign Application Priority Data

Jun. 26, 2014   (JP) ................................ 2014-131221

(51) Int. Cl.
 *A61B 17/04* (2006.01)
 *A61B 17/84* (2006.01)
 *A61F 2/08* (2006.01)
 *A61B 17/86* (2006.01)
 (Continued)

(52) U.S. Cl.
 CPC .......... *A61B 17/866* (2013.01); *A61L 31/022* (2013.01); *A61L 31/148* (2013.01)

(58) Field of Classification Search
None
See application file for complete search history.

(56) References Cited

U.S. PATENT DOCUMENTS

| 2011/0313527 A1 | 12/2011 | Witte et al. |
| 2012/0156477 A1 | 6/2012 | Kurze et al. |
| 2012/0183923 A1 | 7/2012 | Takagi et al. |

(Continued)

FOREIGN PATENT DOCUMENTS

| EP | 2668966 A1 | 12/2013 |
| JP | 2008-125622 A | 6/2008 |

(Continued)

OTHER PUBLICATIONS

International Search Reported dated Apr. 28, 2015 issued in PCT/JP2015/054322.

(Continued)

*Primary Examiner* — Sameh Boles
(74) *Attorney, Agent, or Firm* — Scully, Scott, Murphy & Presser, P.C.

(57) ABSTRACT

An implant including a screw body composed of pure magnesium or a magnesium alloy and having a male thread, and the implant further including an anodized membrane covering an outer surface of the screw body. The male thread has a clearance flank and a pressure flank. The clearance flank faces forward in a traveling direction and the pressure flank faces rearward in the traveling direction during a screwing process of the screw body. The biodegradation period of the anodized membrane on the clearance flank is shorter than the biodegradation period of the anodized membrane on the pressure flank.

5 Claims, 5 Drawing Sheets

(51) Int. Cl.
*A61L 31/02* (2006.01)
*A61L 31/14* (2006.01)

(56) References Cited

U.S. PATENT DOCUMENTS

| 2013/0116696 A1 | 5/2013 | Imwinkelried et al. |
| 2013/0304134 A1 | 11/2013 | Tamai et al. |
| 2016/0053134 A1* | 2/2016 | Kumta ............... A61L 27/04 623/23.72 |

FOREIGN PATENT DOCUMENTS

| JP | 2008-142523 A | 6/2008 |
| JP | 2012-143416 A | 8/2012 |
| JP | 2012-251188 A | 12/2012 |
| JP | 2013-221023 A | 10/2013 |
| JP | 2014-505528 A | 3/2014 |
| WO | WO 2012/088112 A1 | 6/2012 |
| WO | WO 2012/102205 A1 | 8/2012 |
| WO | WO 2013/070669 A1 | 5/2013 |

OTHER PUBLICATIONS

K. Murakami, et al., "Mechanism of Corrosion Protection of Magnesium Alloys Anodized by Phosphate Electrolyte", J. Japan Inst. Metals, 2009, pp. 354-361, vol. 73, No. 5, The Japan Institute of Metals, with English abstract.

P. K. Bowen, et al., "Magnesium in the murine artery: Probing the products of corrosion", Acta Biomaterialia, 2014, pp. 1475-1483, vol. 10, Issue 3., Elsevier Ltd.

* cited by examiner

IMPLANT

This is a continuation of International Application PCT/JP2015/054322 which is hereby incorporated by reference herein in its entirety.

This application is based on Japanese Patent Application No. 2014-131221, the contents of which are incorporated herein by reference.

TECHNICAL FIELD

The present invention relates to implants, and particularly, to a screw-type biodegradable implant for bone fixation.

BACKGROUND ART

A known implant for bone fixation in the related art has a bioabsorbable base material composed of pure magnesium or a magnesium alloy (for example, see Patent Literatures 1 and 2). Since magnesium decomposes by readily reacting with water, the outer surface of the implant is provided with an anodized membrane for the purpose of controlling the biodegradation rate of the implant after being implanted.

CITATION LIST

Patent Literature

{PTL 1}
Japanese Translation of PCT International Application, Publication No. 2014-505528
{PTL 2}
Japanese Unexamined Patent Application, Publication No. 2008-142523

SUMMARY OF INVENTION

Solution to Problem

The present invention provides an implant including a screw body composed of pure magnesium or a magnesium alloy and having a male thread and an anodized membrane covering an outer surface of the screw body. The male thread has a clearance flank and a pressure flank. The clearance flank faces forward in a traveling direction and the pressure flank faces rearward in the traveling direction during a screwing process of the screw body. The biodegradation period of the anodized membrane on the clearance flank is shorter than the biodegradation period of the anodized membrane on the pressure flank.

DESCRIPTION OF EMBODIMENTS

An implant 1 according to an embodiment of the present invention will be described below with reference to the drawings.

Figure 1:
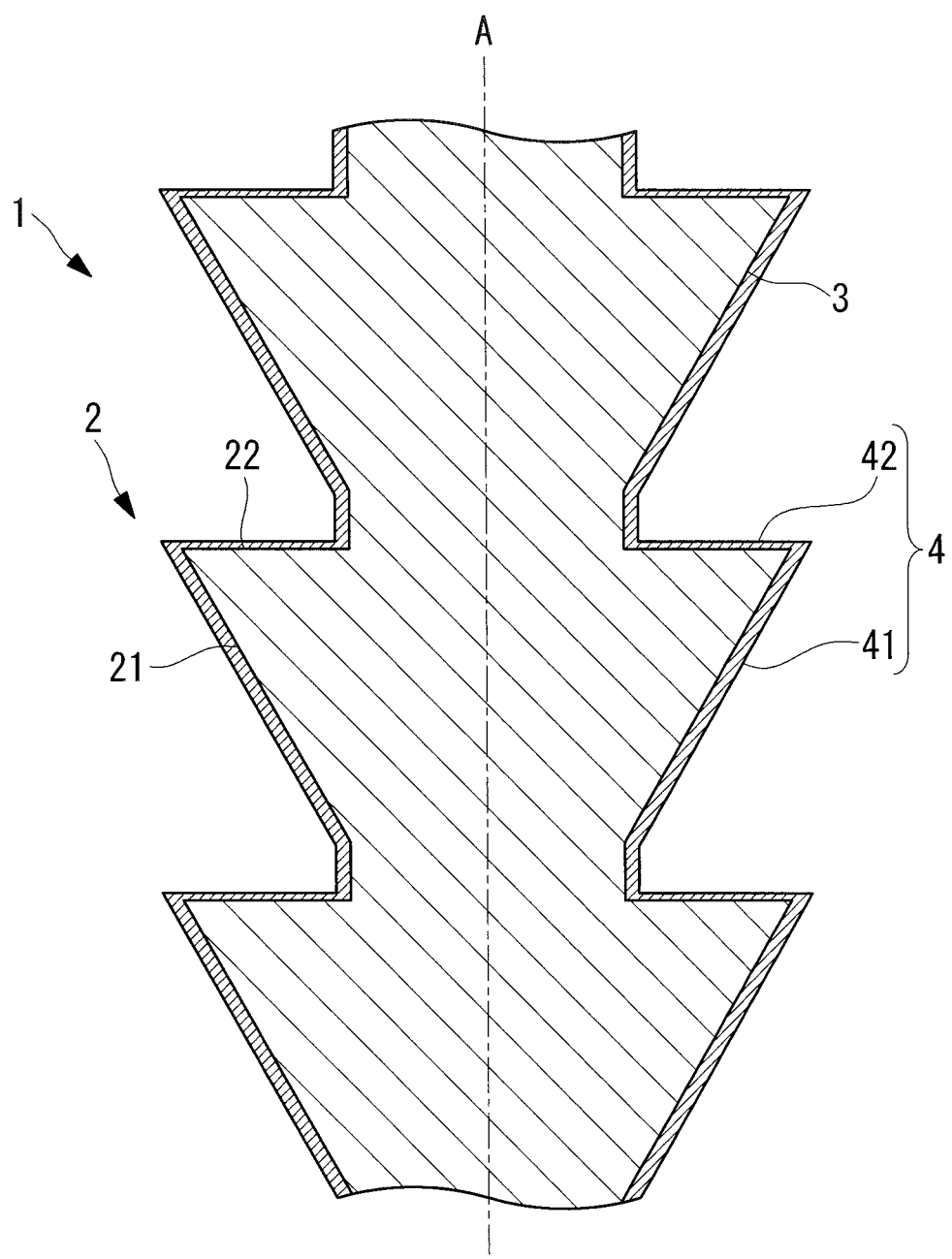
FIG. 1 is a partial vertical sectional view illustrating an implant according to an embodiment of the present invention.

As shown in FIG. 1, the implant 1 according to this embodiment includes a screw body 3 having a male thread 2 and also includes an anodized membrane 4 covering the entire outer surface of the screw body 3.

The screw body 3 is composed of pure magnesium (Mg) or a magnesium alloy having Mg as a main component.

The male thread 2 has a clearance flank 21 and a pressure flank 22 that connect crests and roots. The clearance flank 21 is a surface facing forward in the traveling direction when the screw body 3 is being screwed in, whereas the pressure flank 22 is a surface facing rearward in the traveling direction when the screw body 3 is being screwed in. Although the male thread 2 in this embodiment is assumed to be a buttress thread having the clearance flank 21 inclined relative to a screw axis A and the pressure flank 22 substantially orthogonal to the screw axis A, the shape of the male thread 2 is not limited to this.

Figure 2:
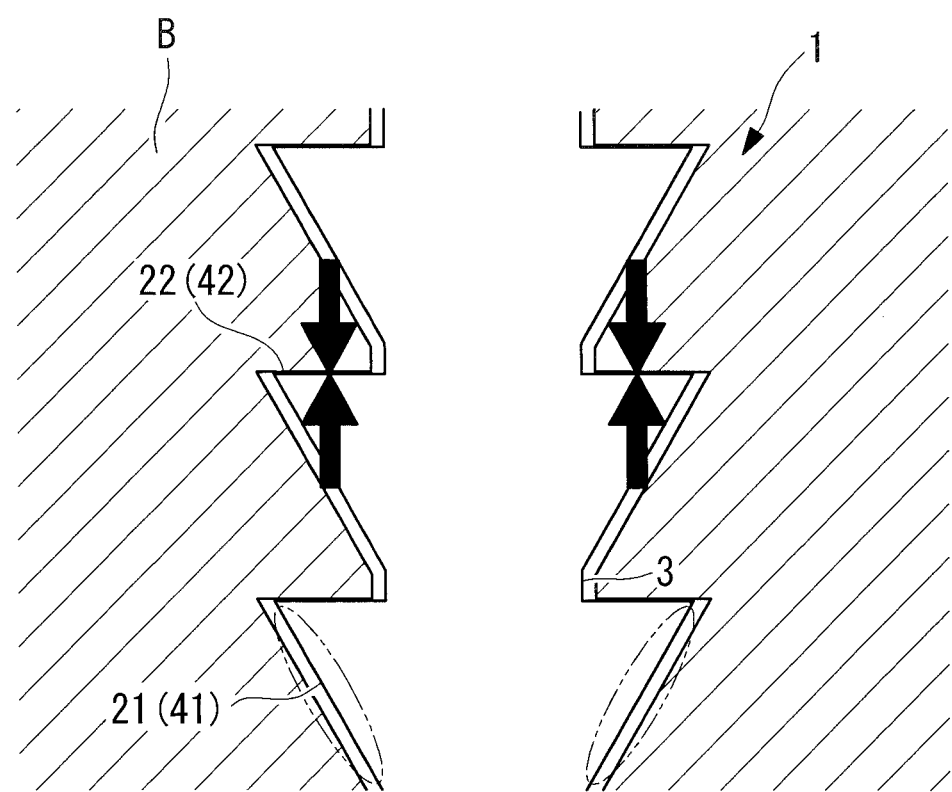
FIG. 2 illustrates the implant in FIG. 1 screwed into a bone.

FIG. 2 illustrates the implant 1 screwed into a bone B. As shown in FIG. 2, in the state where the implant 1 is screwed into the bone B, the pressure flank 22 receives a load (see arrows in the drawing) in the direction of the screw axis A from the bone B. Specifically, a fixation force applied to the bone B by the male thread 2 is exhibited as a result of close contact between the clearance flank 21 and the bone B.

The properties of the anodized membrane 4 vary between that on the clearance flank 21 and that on the pressure flank 22. The biodegradation period of the anodized membrane 4 (also referred to as an anodized membrane 41 hereinafter) on the clearance flank 21 is shorter than the biodegradation period of the anodized membrane 4 (also referred to as an anodized membrane 42 hereinafter) on the pressure flank 22. In detail, the anodized membrane 41 and the anodized membrane 42 are different from each other with respect to the membrane thickness, the average hole diameter, the surface roughness, the phosphorous (P) content, and the carbon (C) content.

With regard to the membrane thickness, the membrane thickness of the anodized membrane 41 on the clearance flank 21 is smaller than the membrane thickness of the anodized membrane 42 on the pressure flank 22.

With regard to the average hole diameter and the surface roughness, the average hole diameter and the maximum surface roughness of the anodized membrane 41 on the clearance flank 21 are respectively larger than the average hole diameter and the maximum surface roughness of the anodized membrane 42 on the pressure flank 22. In detail, the anodized membrane 41 preferably has an average hole diameter ranging between 1 μm and 100 μm inclusive and a maximum surface roughness ranging between 0.4 μm and 10 μm inclusive, and the anodized membrane 42 preferably has an average hole diameter ranging between 0.1 μm and 10 μm inclusive and a maximum surface roughness ranging between 0.01 μm and 1.0 μm inclusive.

The rougher the anodized membrane 4 and the larger the average hole diameter and the maximum surface roughness thereof, the more easily the body fluid ingresses into the anodized membrane 4, thus resulting in an increased corrosion rate of the anodized membrane 4 within the body. Therefore, the anodized membrane 41 on the clearance flank 21 is made to corrode faster than the anodized membrane 42 on the pressure flank 22.

In contrast, the denser the anodized membrane 4 and the smaller the average hole diameter and the maximum surface roughness thereof, the more easily fibrin fibers functioning as an adhesive relative to the bone B are formed on the surface of the anodized membrane 4. In particular, the anodized membrane 4 whose surface has a surface roughness ranging between 1 μm and 2 μm achieves improved wettability and can easily maintain fibrin fibers thereon. Furthermore, the anodized membrane 4 whose surface has a surface roughness ranging between several tens of nanometers and several hundreds of nanometers is known to have an effect of accelerating cell adhesion and increasing secretion of bone activity substances from osteoblastic cells, as well as increasing calcium deposition. Specifically, with the fibrin fibers and bone formation, the pressure flank 22 is securely bonded to the adjacent bone B by means of the anodized membrane 42.

With regard to the P content, the P content of the anodized membrane 42 on the pressure flank 22 is higher than the P content of the anodized membrane 41 on the clearance flank 21. In detail, the anodized membrane 42 preferably has a P content ranging between 10% by weight and 30% by weight inclusive, and the anodized membrane 41 preferably has a P content ranging between 1% by weight and 20% by weight inclusive.

The P in the anodized membrane 4 is derived from phosphoric acid. A higher P content in the anodized membrane 4 accelerates the generation of hydroxyapatite (HA) in accordance with a reaction between phosphoric acid ions and calcium ions in the body fluid at the surface of the anodized membrane 4. Specifically, the generation of HA is accelerated on the anodized membrane 42 on the pressure flank 22 having a high P content, so that a high bonding force between the pressure flank 22 and the bone B is obtained by means of the HA. If the P content is higher than 30% by weight, the content of magnesium oxide and the content of magnesium hydroxide, which have functions for preventing the attack of chlorine ions, become too low, resulting in the possibility of reduced corrosion resistance of the anodized membrane 4.

In contrast, the clearance flank 21 with the low-P-content anodized membrane 4 is less likely to bond with the bone B. Therefore, in a case where the implant 1 has to be removed in the initial implanting stage of the implant 1, the implant 1 can be readily removed. If the P content is lower than 2% by weight, it is difficult to achieve a sufficient sacrificial protection effect with the phosphoric acid.

With regard to the C content, the C content of the anodized membrane 41 on the clearance flank 21 is higher than the C content of the anodized membrane 42 on the pressure flank 22. In detail, the anodized membrane 41 preferably has a C content higher than 0% by weight and lower than 3% by weight, and the anodized membrane 42 preferably has a C content higher than 0% by weight and lower than 1% by weight.

The C contained in the anodized membrane 4 is derived from carbide generated as a result of moisture remaining in the anodized membrane 4 reacting with carbon dioxide in the air. If there is carbide on the outer surface of the implant 1, the hydrophilic properties of the outer surface of the implant 1 deteriorate. This makes it difficult for the blood in the biological organism to come into contact with the implant 1, thus leading to reduced bone conductivity. Specifically, bone formation is accelerated at the anodized membrane 42 having higher hydrophilic properties so that the pressure flank 22 is securely bonded to the adjacent bone B by means of the anodized membrane 42.

Next, a method for manufacturing the implant 1 according to this embodiment will be described.

Figure 3:
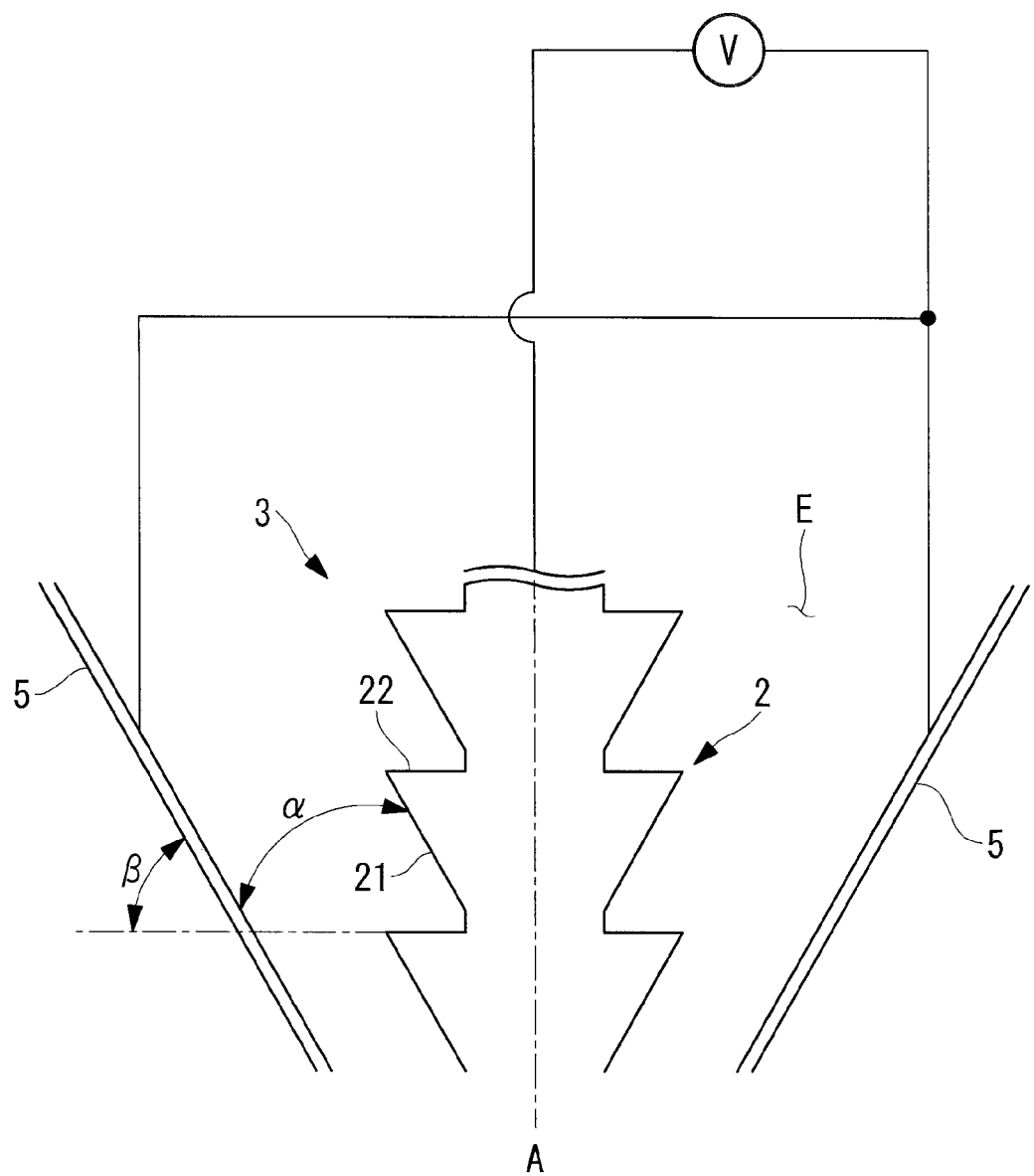
FIG. 3 illustrates an anodizing process in a method for manufacturing the implant in FIG. 1.

As shown in FIG. 3, the method for manufacturing the implant 1 according to this embodiment includes an anodizing process involving anodizing the screw body 3 so as to form the anodized membrane 4 on the entire outer surface of the screw body 3. The anodizing process is performed by immersing the screw body 3 and a cathode 5 composed of, for example, stainless steel into an electrolytic solution E containing phosphoric acid ions and applying a voltage between the screw body 3 and the cathode 5 by using the screw body 3 as an anode.

The cathode 5 is inclined relative to the screw axis A of the screw body 3 such that the distance from the screw axis A gradually decreases toward the distal end (screw end) of the screw body 3. Moreover, an angle a formed between the clearance flank 21 and the cathode 5 is smaller than an angle β formed between the pressure flank 22 and the cathode 5. Such a cathode 5 may be constituted of a plurality of plate-like electrodes disposed facing each other with the screw body 3 interposed therebetween in the radial direction, or may be constituted of a conical-tube-like electrode whose diameter gradually decreases from one end to the other end thereof.

In detail, the angle a formed between the clearance flank 21 and the cathode 5 preferably ranges between 0° and 45° inclusive. In the clearance flank 21, which is substantially parallel to the cathode 5, the electric current easily converges so that the electric current density becomes high, resulting in an increased developing rate of the anodized membrane 41. In the process in which the anodized membrane 41 quickly develops, air bubbles in the electrolytic solution E are easily taken into the anodized membrane 41, so that a rough anodized membrane 41 with a large hole diameter is formed. Furthermore, although the anodized membrane 4 contains Mg, O (oxygen), and P as main components, the electronegativity of O is larger than the electronegativity of P. Thus, between P and O in the electrolytic solution E, a larger amount of O is drawn toward the clearance flank 21. As a result, the component ratio (Mg+O)/P of the anodized membrane 41 is larger than that of the anodized membrane 42.

On the other hand, the angle β formed between the pressure flank 22 and the cathode 5 preferably ranges between 45° and 90° inclusive. In the pressure flank 22 located behind the clearance flank 21 as viewed from the cathode 5, the electric current density is lower than that in the clearance flank 21, resulting in a lower developing rate of the anodized membrane 42. In the process in which the anodized membrane 42 slowly develops, air bubbles in the electrolytic solution E are less likely to be taken into the anodized membrane 42, so that a dense anodized membrane 42 with a small hole diameter is formed. Furthermore, in the pressure flank 22 where the electric current is less likely to converge, it is difficult to take in the O from the electrolytic solution E, so that the component ratio (Mg+O)/P of the anodized membrane 42 is smaller than that of the anodized membrane 41.

When the phosphoric acid concentration of the electrolytic solution E ranges between 0.05 mol/L and 0.2 mol/L inclusive, the electric current density ranges between 10 $A/dm^2$ and 30 $A/dm^2$ inclusive, and the voltage ranges between 350 V and 400 V inclusive, the anodized membranes 41 and 42 having the above-described properties can be respectively formed on the clearance flank 21 and the pressure flank 22 by stopping the electric current between the electrodes.

Figure 4:
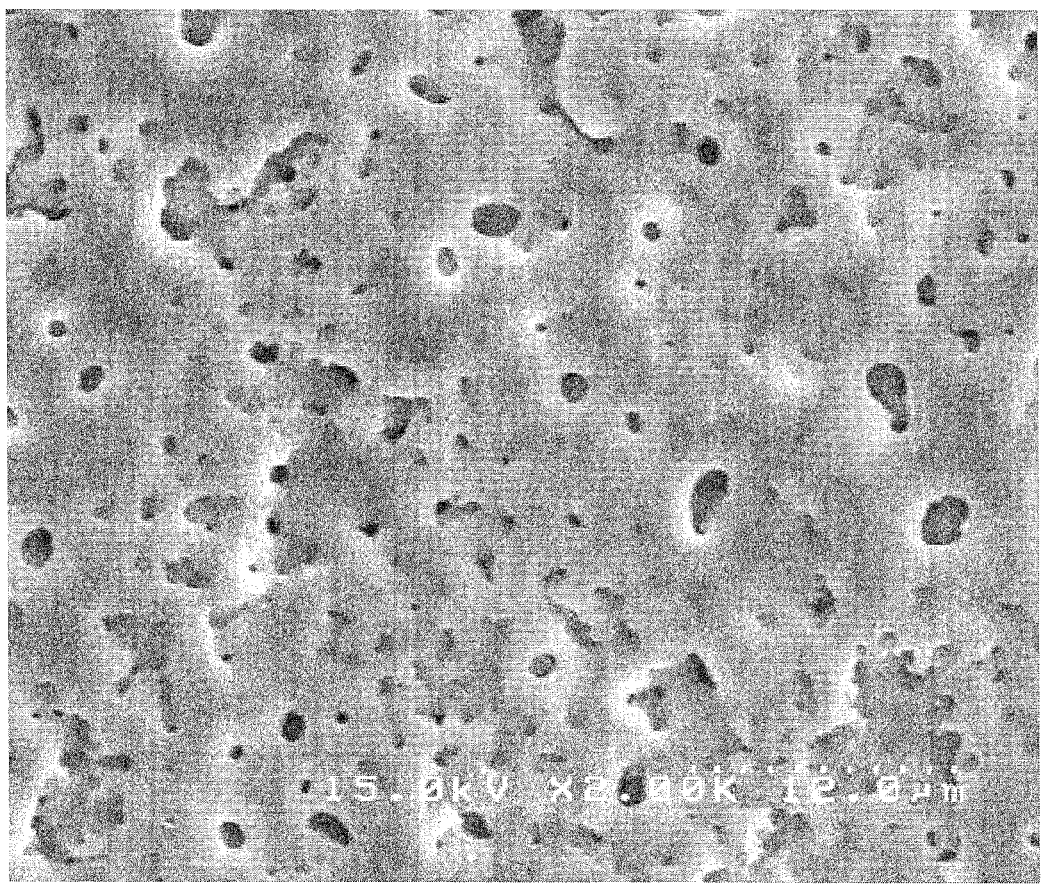
FIG. 4 illustrates a scanning-electron-microscope image showing a cross section of an anodized membrane formed with a high electric current density (voltage: 400 V).
Figure 5:
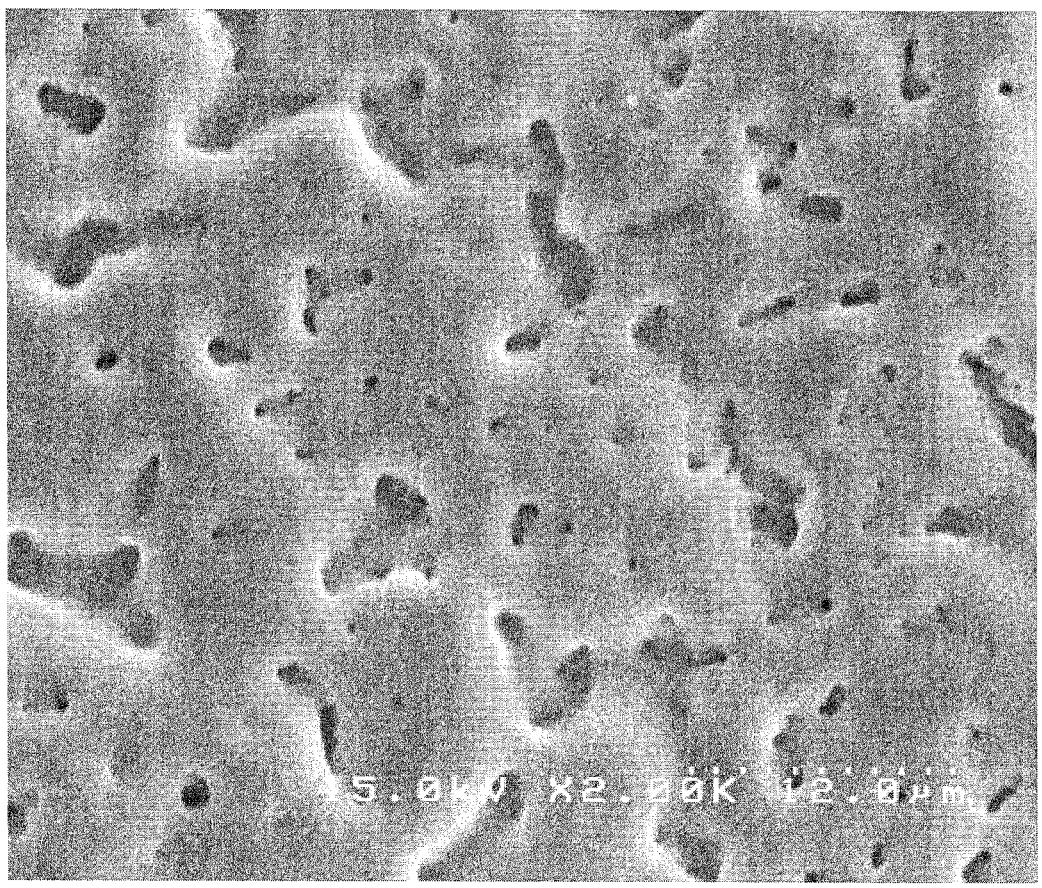
FIG. 5 illustrates a scanning-electron-microscope image showing a cross section of an anodized membrane formed with a low electric current density (voltage: 350 V).

FIGS. 4 and 5 illustrate scanning-electron-microscope images of anodized membranes formed under different electric current densities by varying the applied voltage. Specifically, FIG. 4 illustrates a result obtained by using a voltage of 400 V, and FIG. 5 illustrates a result obtained by using a voltage of 350 V. As shown in FIGS. 4 and 5, a dense anodized membrane having a small hole diameter is formed in the case where the voltage of 350 V is applied rather than in the case where the voltage of 400 V is applied, that is, when the electric current density is lower. It is clear from these results that different anodized membranes 41 and 42 are formed respectively on the clearance flank 21 and the pressure flank 22 with different electric current densities.

Next, the operation of the implant 1 will be described below.

The implant 1 according to this embodiment is a fracture fixation tool for fixing a fractured area and is to be screwed into a hole formed in the bone B. The implant 1 retained in the bone B is protected from rapid corrosion by the anodized membrane 4 covering the outermost side of the implant 1 and is gradually biodegraded.

In this case, the anodized membrane 42 on the pressure flank 22 has a long biodegradation period due to being thick and having a small hole diameter. Therefore, the anodized membrane 42 continues to exist without disappearing at least until the fractured area heals. Moreover, since the anodized membrane 42 has a chemical composition that easily bonds with the bone B, the pressure flank 22 securely bonds with the adjacent bone B.

In contrast, the anodized membrane 41 on the clearance flank 21 has a short biodegradation period due to being thin and having a large hole diameter, and thus disappears at an early stage due to biodegradation. When the anodized membrane 41 disappears and the clearance flank 21 of the screw body 3 becomes exposed, biodegradation of the screw body 3 commences, starting from this exposed area (i.e., an area surrounded by a single-dot chain line in FIG. 2) of the clearance flank 21. However, since the clearance flank 21 does not contribute to the fixation force of the male thread 2 relative to the bone B, the fixation force of the implant 1 relative to the bone B is maintained even if the clearance flank 21 is biodegraded.

Accordingly, in the implant 1 according to this embodiment, the anodized membrane 41 on the clearance flank 21 having no effect on the fixation force relative to the bone B has a short biodegradation period, and the biodegradation of the screw body 3 commences quickly, starting from the clearance flank 21. This is advantageous in that the time it takes for the entire implant 1 to be biodegraded can be shortened while still maintaining the fixation force of the implant 1 relative to the bone, and the implant 1 can be made to disappear quickly after the bone has healed. In particular, secure bonding with the bone B is achieved at the pressure flank 22 exhibiting the fixation force of the implant 1 relative to the bone B, which is advantageous in that the fixation force of the implant 1 relative to the bone B can be maintained at a high level.

The above-described embodiment leads to the following inventions.

The present invention provides an implant including a screw body composed of pure magnesium or a magnesium alloy and having a male thread and an anodized membrane covering an outer surface of the screw body. The male thread has a clearance flank and a pressure flank. The clearance flank faces forward in a traveling direction and the pressure flank faces rearward in the traveling direction during a screwing process of the screw body. The biodegradation period of the anodized membrane on the clearance flank is shorter than the biodegradation period of the anodized membrane on the pressure flank.

According to the present invention, the screw body screwed into the bone of a biological organism is protected from biodegradation by the anodized membrane covering the screw body, so that the fixation force of the male thread relative to the bone can be continuously exhibited over a certain period of time.

In this case, the anodized membrane on the clearance flank of the male thread disappears due to biodegradation at an early stage, so that biodegradation of the screw body commences starting from the clearance flank. However, since the clearance flank does not contribute to the fixation force relative to the bone and the anodized membrane on the pressure flank is still present, the fixation force of the male thread relative to the bone is still maintained even when biodegradation of the clearance flank commences.

Consequently, the implant can quickly disappear after the bone has healed while still maintaining a high fixation force relative to the bone until the bone has healed.

In the above invention, an average hole diameter of the anodized membrane on the clearance flank is preferably larger than an average hole diameter of the anodized membrane on the pressure flank. Furthermore, it is more preferable that the average hole diameter of the anodized membrane on the clearance flank range between 1 µm and 100 µm inclusive, and that the average hole diameter of the anodized membrane on the pressure flank range between 0.1 µm and 10 µm inclusive.

The larger the average hole diameter of the anodized membrane, the more easily the body fluid ingresses into the anodized membrane, thus resulting in an increased biodegradation rate of the anodized membrane. In contrast, the smaller the average hole diameter of the anodized membrane, the more easily fibrin fibers are formed on the surface thereof, thus resulting in an increased bonding force relative to the bone. Therefore, by designing the average hole diameter of the anodized membrane on each flank in the above-described manner, the biodegradation period of the anodized membrane on the clearance flank can be shortened, while the bonding force between the pressure flank and the bone can be increased.

In the above invention, the phosphorous content of the anodized membrane on the pressure flank is preferably higher than the phosphorous content of the anodized membrane on the clearance flank. Furthermore, it is more preferable that the phosphorous content of the anodized membrane on the pressure flank range between 10% by weight and 30% by weight inclusive, and that the phosphorous content of the anodized membrane on the clearance flank range between 2% by weight and 20% by weight inclusive.

A higher phosphorous content in the anodized membrane accelerates the generation of hydroxyapatite (HA) on the anodized membrane, so that the bonding force between the flank and the bone is increased by means of HA. Therefore, by designing the phosphorous content of the anodized membrane on each flank in the above-described manner, the bonding force between the pressure flank and the bone can be increased, while the bonding between the clearance flank and the bone can be suppressed.

REFERENCE SIGNS LIST 1 implant
2 male thread
21 clearance flank
22 pressure flank
3 screw body
4, 41, 42 anodized membrane
5 cathode
A screw axis
B bone
E electrolytic solution

The invention claimed is:

1. An implant comprising:
a screw body composed of pure magnesium or a magnesium alloy and having a male thread; and
an anodized membrane covering an outer surface of the screw body,
wherein the male thread has a clearance flank and a pressure flank, the clearance flank facing forward in a traveling direction and the pressure flank facing rearward in the traveling direction during a screwing process of the screw body, and
wherein a biodegradation period of the anodized membrane on the clearance flank is shorter than a biodegradation period of the anodized membrane on the pressure flank.

2. The implant according to claim 1,
wherein an average hole diameter of the anodized membrane on the clearance flank is larger than an average hole diameter of the anodized membrane on the pressure flank.

3. The implant according to claim 2,
wherein the average hole diameter of the anodized membrane on the clearance flank ranges between 1 μm and 100 μm inclusive, and
wherein the average hole diameter of the anodized membrane on the pressure flank ranges between 0.1 μm and 10 μm inclusive.

4. The implant according to claim 1,
wherein the phosphorous content of the anodized membrane on the pressure flank is higher than the phosphorous content of the anodized membrane on the clearance flank.

5. The implant according to claim 4,
wherein the phosphorous content of the anodized membrane on the pressure flank ranges between 10% by weight and 30% by weight inclusive, and
wherein the phosphorous content of the anodized membrane on the clearance flank ranges between 2% by weight and 20% by weight inclusive.

* * * * *